United States Patent
Dominguez et al.

(10) Patent No.: US 11,186,569 B2
(45) Date of Patent: Nov. 30, 2021

(54) OPTICAL BRIGHTENER FOR WHITENING PAPER

(71) Applicant: Archroma IP GmbH, Reinach (CH)

(72) Inventors: Cristina Dominguez, Saint-Louis (FR); Andrew Jackson, Muenchenstein (CH); David Atkinson, Arlesheim (CH); Meral Ilhan, Hirsingue (FR); Marc Bukowski, Rheinfelden (DE)

(73) Assignee: Archroma IP GmbH, Reinach (CH)

( * ) Notice: Subject to any disclaimer, the term of this patent is extended or adjusted under 35 U.S.C. 154(b) by 0 days.

(21) Appl. No.: 16/759,756

(22) PCT Filed: Dec. 14, 2018

(86) PCT No.: PCT/EP2018/085029
§ 371 (c)(1),
(2) Date: Apr. 28, 2020

(87) PCT Pub. No.: WO2019/121411
PCT Pub. Date: Jun. 27, 2019

(65) Prior Publication Data
US 2020/0331895 A1    Oct. 22, 2020

(30) Foreign Application Priority Data
Dec. 22, 2017 (EP) .................................. 17210363

(51) Int. Cl.
*C07D 403/12* (2006.01)
*D21H 17/09* (2006.01)
*D21H 21/32* (2006.01)

(52) U.S. Cl.
CPC .......... *C07D 403/12* (2013.01); *D21H 17/09* (2013.01); *D21H 21/32* (2013.01)

(58) Field of Classification Search
CPC ....... C07D 403/12; D21H 17/09; D21H 21/32
See application file for complete search history.

(56) References Cited

U.S. PATENT DOCUMENTS

| 6,331,626 | B1 | 12/2001 | Rohringer et al. | |
|---|---|---|---|---|
| 7,198,731 | B2* | 4/2007 | Jackson | C09K 11/06 252/301.23 |
| 2003/0236326 | A1 | 12/2003 | Drenker et al. | |
| 2005/0022320 | A1* | 2/2005 | Jackson | D06L 4/621 8/516 |

FOREIGN PATENT DOCUMENTS

| EP | 2192230 | * | 11/2008 | ............. D21H 21/30 |
|---|---|---|---|---|
| EP | 2192230 | A1 | 6/2010 | |
| WO | 9842685 | A1 | 10/1998 | |
| WO | 03044275 | A1 | 5/2003 | |
| WO | 2011098237 | A1 | 8/2011 | |
| WO | 2016142955 | A1 | 9/2016 | |

OTHER PUBLICATIONS

European Patent Office, Search Report and Written Opinion issued in PCT/EP2018/085029 dated Feb. 15, 2019, 11 pages.

* cited by examiner

*Primary Examiner* — Amina S Khan
(74) *Attorney, Agent, or Firm* — Wood Herron & Evans LLP

(57) ABSTRACT

The invention relates to an optical brightener for whitening and brightening of paper, board, textiles and non-wovens, a process for manufacturing said optical brightener, the use of said brightener in paper making processes and a process for whitening paper.

8 Claims, No Drawings

OPTICAL BRIGHTENER FOR WHITENING PAPER

BACKGROUND OF THE INVENTION

The instant invention relates to an optical brightener for whitening and brightening of paper, board, textiles and non-wovens, a process for manufacturing said optical brightener, the use of said brightener in paper making processes and a process for whitening paper.

A high level of whiteness (usually referred to as CIE Whiteness) and brightness (for example, ISO Brightness) are important parameters for evaluating the quality of cellulosic substrates, in particular paper products for the end-user. The most important raw materials for such products are cellulose, pulp and lignin. These raw materials, however, naturally absorb blue light and are therefore yellowish in color and impart a dull appearance to the products.

In order to compensate for the natural absorption of the blue light by the raw materials, optical brighteners (also referred to as optical brightening agents or OBAs, or fluorescent whitening agents or FWAs) are used. OBAs typically absorb UV-light with a maximum wavelength of 350 nm to 360 nm and convert this absorbed light into visible blue light with a maximum wavelength of 440 nm.

The optical characteristics of products formed from cellulosic substrates are evaluated according to known standard procedures of CIE Whiteness and ISO Brightness measurement. The CIE Whiteness value is derived from measurements of the light reflected by the paper across the whole of visible light spectrum. Brightness is the measurement of the amount of reflectance of blue light.

It is known in the state of the art to apply optical brighteners (OBAs) by means of different procedures to paper, board, textile and non-woven products to enhance the whiteness, brightness and thus attractiveness of these products. The most widely-used optical brighteners in these industries are anilino-substituted bistriazinyl derivatives of 4,4'-diaminostilbene-2,2'-disulphonic acid.

In the paper industry the most widely used OBA is that of formula (1). The OBA of formula (1) offers the flexibility of application at any point in the paper making machine, either at the wet end (application to paper stock) or to the surface of the paper using either sizing or coating techniques. Other OBAs in which the anilino-substituent contains two sulphonic acid groups afford a particularly high whiteness when applied to the surface of paper.

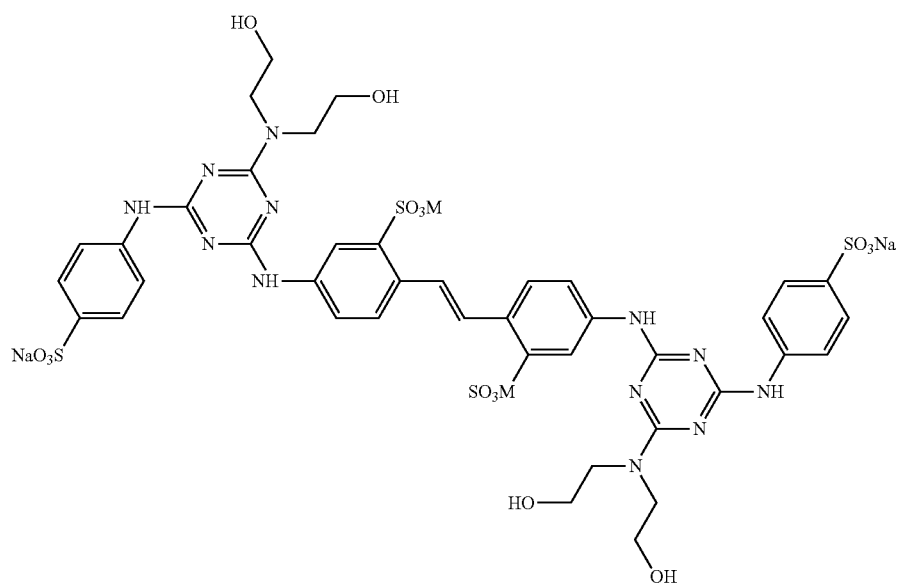

(1)

EP 0884312 A1 discloses a formulation comprising a fluorescent whitening agent which has an active substance concentration of more than 30% by weight. The active substance is a hydrate of 4,4'-di-triazinylamino-2,2'-di-sulphostilbene which carries no substituents at the terminal anilino-substituent.

WO 2010/060570 A1 discloses an optical brightening composition comprising an OBA of the bis(triazinylamino) stilbene type containing two sulpho groups at the terminal anilino-substituent. This whitening agent enables good compatibility with sizing compositions containing divalent metal salts.

There is a continuing demand in the paper industry to provide improved OBAs and OBA compositions. It has therefore been an object to provide OBAs which are capable of delivering whiteness and brightness at a greater efficiency, with consequent benefits of improved sustainability and reduced costs, while maintaining good affinity to cellulosic substrates like paper and board.

SUMMARY OF THE INVENTION

In a first aspect of the invention the object is solved by a compound of formula (2)

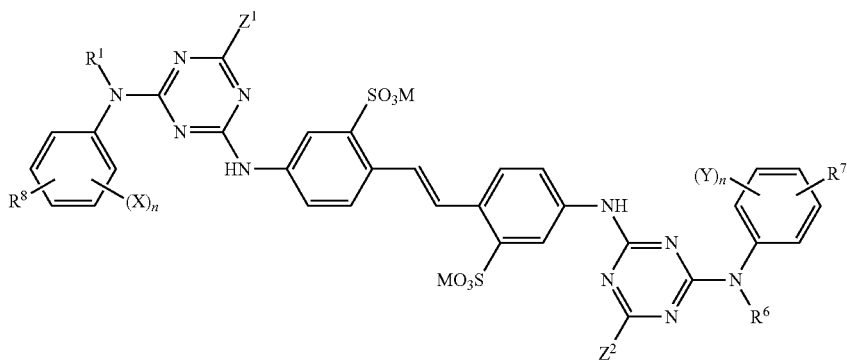

(2)

in which
$Z^1$ and $Z^2$ signify independently from each other $OR^9$ or $OR^{10}$, wherein
  $R^9$ and $R^{10}$ signify independently from each other linear $C_1$ to $C_3$ alkyl or branched $C_3$ alkyl, or
$Z^1$ and $Z^2$ signify independently from each other $NR^2R^3$ or $NR^4R^5$, wherein
  $R^2$ and $R^4$ signify independently from each other hydrogen, linear $C_1$ to $C_4$ alkyl or branched $C_3$, $C_4$ alkyl, linear $C_2$ to $C_3$ hydroxyalkyl or branched $C_3$ hydroxyalkyl, $CH_2CO_2M$, $CH_2CH_2CONH_2$ or $CH_2CH_2CN$,
  $R^3$ and $R^5$ signify independently from each other, linear $C_1$ to $C_4$ alkyl or branched $C_3$, $C_4$ alkyl, linear $C_2$ to $C_3$ hydroxyalkyl or branched $C_3$ hydroxyalkyl, $CH_2CH_2SO_3M$ $CH_2CO_2M$, $CH(CO_2M)CH_2CO_2M$ or $CH(CO_2M)CH_2CH_2CO_2M$, benzyl, or
$R^2$ and $R^3$
and/or
$R^4$ and $R^5$ signify together with their neighboring nitrogen atom a morpholine ring, and
$R^1$ and $R^6$ signify independently from each other hydrogen, linear $C_1$ to $C_4$ alkyl or branched $C_3$, $C_4$ alkyl, linear $C_2$ to $C_3$ hydroxyalkyl or branched $C_3$ hydroxyalkyl, $CH_2CH_2CONH_2$ or $CH_2CH_2CN$,
$R^7$ and $R^8$ signify independently from each other hydrogen, linear $C_1$ to $C_4$ alkyl or branched $C_3$, $C_4$ alkyl, under the proviso that at least one of $R^7$ or $R^8$ is, linear $C_1$ to $C_4$ alkyl or branched $C_3$, $C_4$ alkyl,
X and Y signify independently from each other $CO_2M$ or $SO_3M$, m and n are 0, 1 or 2, under the proviso that at least one of m or n is at least 1, and
M signifies a cation for balancing the anionic charge selected from the group comprising or essentially consisting of hydrogen, an alkali metal cation, alkaline earth metal cation, ammonium, ammonium which is mono-, di-, tri- or tetrasubstituted by a linear $C_1$ to $C_4$ alykla or branched $C_3$, $C_4$ alkyl radical, ammonium which is mono-, di-, tri- or tetrasubstituted by a linear $C_1$ to $C_4$ hydroxyalkyl or branched hydroxyalkyl radical, ammonium which is di-, tri-, or tetrasubstituted by a mixture of linear $C_1$ to $C_4$ alkyl or branched $C_3$, $C_4$ alkyl radical or linear $C_1$ to $C_4$ hydroxyalkyl or branched $C_3$, $C_4$ hydroxyalkyl radical or mixtures of said cations,
wherein if $R^7$ is, linear $C_1$ to $C_4$ alkyl or branched $C_3$, $C_4$ alkyl, then n is at least 1, and/or if $R^8$ is, linear $C_1$ to $C_4$ alkyl or branched $C_3$, $C_4$ alkyl, then m is at least 1.

Preferably, according to the first aspect of the invention $R^7$ and/or $R^8$ signify hydrogen, methyl or ethyl, preferably one or both of $R^7$ and $R^8$ is in para position to the $R^1$ or respectively $R^6$ carrying nitrogen atom, under the proviso that at least one of $R^7$ or $R^8$ is methyl or ethyl.

Preferably, according to the first aspect of the invention $R^7$ and/or $R^8$ signify methyl, preferably one or both of $R^7$ and $R^8$ is in para position to the $R^1$ respectively $R^6$ carrying nitrogen atom.

Preferably, according to the first aspect of the invention X and Y signify $SO_3M$, and
M signifies a cation for balancing the anionic charge selected from the group of $Li^+$, $Na^+$, $K^+$, ½ $Ca^{2+}$, ½ $Mg^{2+}$, ammonium which is mono-, di-, tri-, or tetrasubstituted by a linear $C_1$ to $C_4$ hydroxyalkyl or branched $C_3$, $C_4$ hydroxyalkyl radical, ammonium which is di-, tri-, or tetrasubstituted by a mixture of linear $C_1$ to $C_4$ alkyl or branched $C_3$, $C_4$ alkyl radical and linear $C_1$ to $C_4$ hydroxyalkyl or branched $C_3$, $C_4$ hydroxyalkyl radical or mixtures of said cations, and
m and n is 1,
or wherein
X and Y signify $SO_3M$, and
M signifies $Na^+$, and
m and n is 1.

Preferably, according to the first aspect of the invention X is in meta position to the $R^1$ carrying nitrogen atom and Y is in meta position to the $R^6$ carrying nitrogen atom.

Preferably, according to the first aspect of the invention $R^9$ and $R^{10}$ signify independently from each other methyl, ethyl, propyl or isopropyl, preferably methyl.

Preferably, according to the first aspect of the invention $R^1$ and/or $R^6$ signify hydrogen.

Preferably, according to the first aspect of the invention $R^2$ and $R^4$
and/or
$R^3$ and $R^5$ signify independently from each other hydroxyethyl and/or hydroxyisopropyl, preferably hydroxyethyl.

In a second aspect the invention relates to a concentrated aqueous composition comprising 5 to 60% by weight of at least one compound of formula (2) according to at least embodiment of the first aspect of the invention.

Preferably, according to the second aspect of the invention the concentrated aqueous composition comprises one or more additives of biocides, thickeners, shading colorants, solubilizers, polymers such as, poly(vinyl alcohol) and polyethylene glycol, or inorganic salt such as sodium chloride.

Preferably, according to the second aspect of the invention the concentrated aqueous composition is in the form of a slurry.

In a third aspect the invention relates to a process for the preparation of a compound of formula (2) according to at least one embodiment according to the first aspect of the invention, wherein cyanuric halide is reacted in a first step with a compound of formula (4) and/or a compound of formula (5)

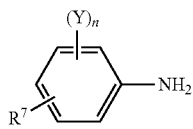

(4)

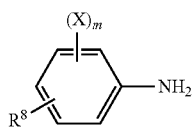

(5)

wherein
$R^7$, $R^8$, X, Y, m and n have the meaning as defined in at least one embodiment according to the first aspect of the invention, and wherein the reaction product of the first step is reacted in a second step with
a compound of the formula (6)

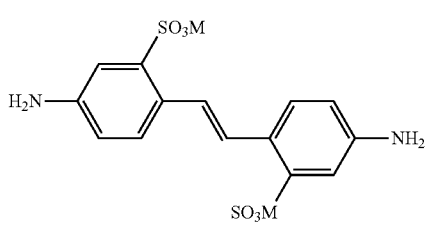

(6)

wherein M has the meaning as defined in at least of the embodiments defined above,
or wherein cyanuric halide is reacted in a first step with a compound of formula (6) and the resultant of the first step is reacted in a second step with compounds of formula (4) and/or formula (5),
and wherein the reaction product of the second step is reacted in a third step with
a compound of formula (7) and/or a compound of formula (8)

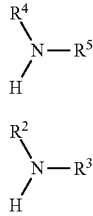

(7)

(8)

wherein $R^2$, $R^3$, $R^4$, $R^5$ have the meaning as defined before,
or
wherein the reaction product of the second step is reacted in a third step with a compound of formula (9) and/or a compound of formula (10)

$$H\text{---}OR^9 \qquad (9)$$

$$H\text{---}OR^{10} \qquad (10)$$

wherein $R^9$ and $R^{10}$ have the meaning as defined above.

Preferably, according to the third aspect of the invention the reaction is carried out in an aqueous medium and the first step is carried out at a temperature in the range of 0° C. to 20° C. and at a pH value in the range of pH=4 to 6, the second step is carried out at a temperature in the range of 20 to 80° C. and at a pH value in the range of pH=6 to 7.5, and the third step is carried out at a temperature in the range of 60° C. to 102° C. and at a pH value in the range of pH=7.5 to 9.

In a fourth aspect the invention relates to a process for whitening paper comprising the steps:
providing a suspension of pulp,
adding 0.01 to 5% by weight based on dry fiber of the pulp of an aqueous composition according to at least one embodiment of the second aspect of the invention to obtain a brightened pulp,
draining water of the blend,
pressing and drying the blend into paper sheet.

In a fifth aspect the invention relates to a composition for surface brightening of paper comprising at least one surface sizing agent, and at least one compound of formula (2) according to at least one of the embodiments of the first aspect of the invention and water.

Preferably, according to the fifth aspect of the invention the surface sizing agent comprises one or more starch materials.

Preferably, according to the fifth aspect of the invention the one or more starch materials are selected from the group consisting of enzymatically, chemically or thermally modified starch, oxidized starch, hydroxyethylated starch, acetylated starch, native starch, anionic starch, cationic starch or amphiphilic starch.

Preferably, according to the fifth aspect of the invention the amount of the surface sizing agent in the surface brightening composition is between 1% and 30% by weight, preferably 2 and 20% by weight, more preferably 5 to 15% by weight, the weight % being based on the total weight of the surface brightening composition.

Preferably, according to the fifth aspect of the invention the pH value of the surface brightening composition is in the range of 4 to 13, preferably 6 to 11.

In a sixth aspect the invention relates to the preparation of a surface brightening composition by adding the compound of formula (2) according to at least one embodiment of the first aspect of the invention as an optical brightening agent to a preformed aqueous solution of the surface sizing agent at a temperature of between 20° C. and 90° C.

In a seventh aspect the invention relates to a pigmented coating composition comprising at least one pigment, at least one binder, at least one compound of formula (2) according to at least one embodiment of the first aspect of the invention and water.

Preferably, according to the seventh aspect of the invention the pigmented coating composition comprises 10 to 70% by weight, preferably 40 to 60% by weight of at least one white pigment, the weight % being based on the total weight of the pigmented coating composition.

Preferably, according to the seventh aspect of the invention the pigmented coating composition comprises 0.01 to 1% by weight, preferably 0.05 to 0.5% by weight of the compound of formula (2) according to at least one embodiment of the first aspect of the invention, the % by weight being based on the total weight of the dry weight white pigment in the pigmented coating composition.

Preferably, according to the seventh aspect of the invention the white pigment is selected from the group consisting of aluminum silicates, calcium carbonate, titanium dioxide, aluminum hydroxide, barium carbonate, barium sulphate and calcium sulphate or mixtures thereof.

Preferably, according to the seventh aspect of the invention the binder is selected from a primary binder comprising one or more of synthetic latex, styrene-butadiene, vinylacetate, styrene acrylic, vinyl acrylic, or ethylene vinyl acetate polymer and optionally a secondary binder comprising one or more of starch, carboxymethylcellulose, casein, soy polymer, polyvinyl alcohol.

In an eighth aspect the invention relates to a detergent composition comprising one or more surfactants and at least one compound of formula (2) according to one embodiment according to the first aspect of the invention.

Preferably, according to the eighth aspect of the invention the detergent composition is in liquid form and the amount of the compound of formula (2) is between 0.005 to 1% by weight, preferably between 0.01 to 0.5% by weight most preferably between 0.02 to 0.25% by weight. The weight % being based on the total weight of the detergent composition.

Preferably, according to the eighth aspect of the invention the detergent composition comprises further builders, selected from the group consisting of alkali metal polyphosphate, sodium carbonate and zeolites, anti-redeposition agents selected from carboxymethylcellulose and poly(vinylpyrrolidone) and enzymes selected from protease, amylases and lipases.

In a ninth aspect the invention relates to the use of compounds of formula (2) according to at least one embodiment of the first aspect of the invention or to the use of an aqueous composition according to at least one embodiment of the second aspect of the invention for optical brightening of textiles, paper, board and non-wovens.

Preferably, according to the ninth aspect the invention relates to the use of compound of formula (2) according to at least one embodiment of the first aspect of the invention in a paper making process wherein the compound of formula (2) is added to pulp.

Preferably, according to the ninth aspect the invention relates to the use of compounds of formula (2) according to at least one embodiment of the first aspect of the invention in a composition for surface brightening of paper according to at least one embodiment according to the fifth aspect of the invention, or in a pigmented coating composition according to at least one embodiment of the seventh aspect of the invention, or in a detergent composition according to at least one embodiment according to the eighth aspect of the invention.

DESCRIPTION OF THE INVENTION

In a first aspect the instant invention relates to a compound of formula (2)

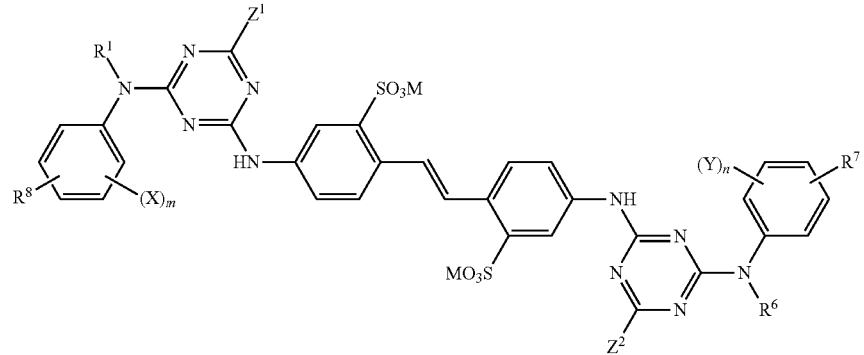

(2)

in which
$Z^1$ and $Z^2$ signify independently from each other $OR^9$ or $OR^{10}$, wherein
$R^9$ and $R^{10}$ signify independently from each other linear $C_1$ to $C_3$ alkyl or branched $C_3$ alkyl, or
$Z^1$ and $Z^2$ signify independently from each other $NR^2R^3$ or $NR^4R^5$, wherein
$R^2$ and $R^4$ signify independently from each other hydrogen, linear $C_1$ to $C_4$ alkyl or branched $C_3$, $C_4$ alkyl, linear $C_2$, $C_3$ hydroxyalkyl or branched $C_3$ hydroxyalkyl, $CH_2CO_2M$, $CH_2CH_2CONH_2$ or $CH_2CH_2CN$,
$R^3$ and $R^5$ signify independently from each other linear or branched $C_1$ to $C_4$ alkyl, linear $C_2$ to $C_3$ hydroxyalkyl or branched $C_3$ hydroxyalkyl, $CH_2CH_2SO_3M$ $CH_2CO_2M$, $CH(CO_2M)CH_2CO_2M$ or $CH(CO_2M)CH_2CH_2CO_2M$, benzyl, or $R^2$ and $R^3$ and/or $R^4$ and $R^5$ signify together with their neighboring nitrogen atom a morpholine ring, and $R^1$ and $R^6$ signify independently from each other hydrogen, linear $C_1$ to $C_4$ alkyl or branched $C_3$, $C_4$ alkyl, linear $C_2$ to $C_3$ hydroxyalkyl or branched $C_3$ hydroxyalkyl, $CH_2CH_2CONH_2$ or $CH_2CH_2CN$, $R^7$ and $R^8$ signify independently from each other hydrogen, linear $C_1$ to $C_4$ alkyl or branched $C_3$, $C_4$ alkyl, under the proviso that at least one of $R^7$ or $R^8$ is linear $C_1$ to $C_4$ alkyl or branched $C_3$, $C_4$ alkyl, X and Y signify independently from each other $CO_2M$ or $SO_3M$, m and n are 0, 1 or 2, under the proviso that at least one of m or n is at least 1, and M signifies a cation for balancing the anionic charge selected from the group comprising or essentially consisting of hydrogen, an alkali metal cation, alkaline earth metal cation, ammonium, ammonium which is mono-, di-, tri- or tetrasubstituted by a linear $C_1$ to $C_4$ alkyl or branched $C_3$, $C_4$ alkyl radical, ammonium which is mono-, di-, tri- or tetrasubstituted by a or linear $C_1$ to $C_4$ hydroxyalkyl or branched $C_3$, $C_4$ hydroxyalkyl radical, ammonium which is di-, tri-, or tetrasubstituted by a mixture of linear $C_1$ to $C_4$ alkyl or branched $C_3$, $C_4$ alkyl radical or linear $C_1$ to $C_4$ hydroxyalkyl or branched $C_3$, $C_4$ hydroxyalkyl radical or mixtures of said cations, wherein if $R^7$ is linear $C_1$ to $C_4$ alkyl or branched $C_3$, $C_4$ alkyl, then n is at least 1, and/or if $R^8$ is linear $C_1$ to $C_4$ alkyl or branched $C_3$, $C_4$ alkyl, then m is at least 1.

The compound of formula (2) has surprisingly good whitening and brightening effects while maintaining a good affinity to cellulosic fibers. Thus, smaller amounts of the compound of formula (2) are needed to achieve the required whitening effects on paper or board with consequent benefits of improved sustainability and reduced costs.

Within the present application the compound of formula (2) is termed an optical brightening agent (OBA).

In this respect the inventors found that if at least one terminal anilino-substituent in the compound of formula (2) carries a linear or branched $C_1$ to $C_4$ alkyl group and at least one $SO_3M$ or $CO_2M$ group at the same time the OBA quality in respect of whitening and brightening performance is improved.

The compound of formula (2) may be applied to cellulosic fiber either by addition to paper stock, or by treatment of the paper surface in a sizing or coating composition.

In certain embodiments the compound of formula (2) is characterized in that $R^9$ or $R^{10}$ signify independently from each other methyl, ethyl, propyl, branched propyl, butyl or branched butyl. In further embodiments $R^9$ and $R^{10}$ are the same, preferably both $R^9$ and $R^{10}$ signify methyl, i.e. $Z^1$ and $Z^2$ signify $O—CH_3$.

Preferably, the compound of formula (2) is characterized in that $R^7$ and/or $R^8$ are hydrogen, methyl or ethyl, preferably one or both of $R^7$ and $R^8$ is in the para position to the $R^1$ respectively $R^6$ carrying nitrogen atom under the proviso that at least one of $R^7$ or $R^8$ is methyl or ethyl.

Preferably, the compound of formula (2) is characterized in that $R^7$ and/or $R^8$ signify methyl, and preferably one or both of $R^7$ and $R^8$ is in the para position to the $R^1$ respectively $R^6$ carrying nitrogen atom. It has surprisingly been found that the affinity and substantivity to cellulosic fiber is improved when $R^7$ and $R^8$ is methyl.

According to one embodiment of the first aspect of the invention the sum of m and n is 2, 3 or 4. In one embodiment, m=n=2 is excluded. Preferred is m=n=1.

Preferably, the compound of formula (2) is characterized in that

X and Y signify $SO_3M$, and

M signifies a cation for balancing the anionic charge selected from the group of $Li^+$, $Na^+$, $K^+$, ½ $Ca^{2+}$, ½ $Mg^{2+}$, ammonium which is mono-, di-, tri- or tetrasubstituted by a linear $C_1$ to $C_4$ alkyl or branched $C_3$, $C_4$ alkyl radical, ammonium which is mono-, di-, tri- or tetrasubstituted by a or linear $C_1$ to $C_4$ hydroxyalkyl or branched $C_3$, $C_4$ hydroxyalkyl radical, ammonium which is di-, tri-, or tetrasubstituted by a mixture of linear $C_1$ to $C_4$ alkyl or branched $C_3$, $C_4$ alkyl radical or linear $C_1$ to $C_4$ hydroxyalkyl or branched $C_3$, $C_4$ hydroxyalkyl radical, and m and n is 1, or wherein X and Y signify $SO_3M$, and M signifies $Na^+$, $K^+$, $Li^+$, trimethylammonium and dimethylethanolammonium, and m and n is 1.

Within the present application the term "½ $Ca^{2+}$" and "½ $Mg^{2+}$" represents a formal notation to represent the balanced stoichiometry of cationic and anionic charges within the compound of formula (2). Effectively, one divalent calcium or magnesium cation compensates two anionic charges originating from one or two compounds of formula (2).

Preferably, the compound of formula (2) is characterized in that X is in meta position to the $R^1$ carrying nitrogen atom and Y is in meta position to the $R^6$ carrying nitrogen atom.

Preferably, the compound of formula (2) is characterized in that $R^1$ and/or $R^6$ signify hydrogen.

Preferably, the compound of formula (2) is characterized in that $R^2$ and $R^4$ and/or $R^3$ and $R^5$ signify independently from each other hydroxyethyl and/or hydroxyisopropyl, preferably hydroxyethyl.

In a second aspect the invention relates to an aqueous composition comprising or consisting of 5 to 60% by weight referred to the total weight of the aqueous composition of at least one compound of formula (2).

Preferably, the amount of compound of formula (2) in the aqueous composition is at least 7.5% by weight, or at least 10% by weight, or at least 12.5% by weight or at least 15% by weight, and at most 55% by weight, or at most 50% by weight, or at most 45% by weight, or at most 40% by weight, preferably between 7.5 and 55% by weight, or between 10 and 50% by weight, or between 12.5 and 45% by weight, or between 15 and 40% by weight, wherein the % by weight is based on the total weight of the aqueous composition.

The aqueous composition according to the invention can contains one or more additives selected from biocides, thickeners, shading colorants, solubilizers, polymers such as poly(vinyl alcohol) and polyethylene glycol, or inorganic salt such as sodium chloride.

The term "aqueous composition" as used within the context of the present application refers to a water-based composition, i.e. the composition comprises water.

In a third aspect the invention relates to a process for the preparation of a compound of formula (2) according to any embodiment according to the first aspect of the invention. The process is characterized in that cyanuric halide is reacted in a first step with a compound of formula (4) and/or a compound of formula (5)

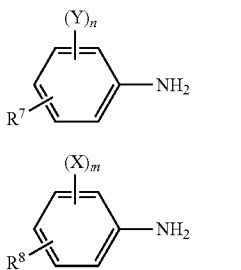

(4)

(5)

wherein
$R^7$, $R^8$, X, Y, m and n have the meaning as defined before and wherein the reaction product of the first step is reacted in a second step with
a diamine compound of the formula (6)

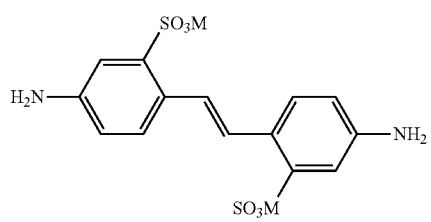

(6)

wherein M has the meaning as defined before,
or wherein cyanuric halide is reacted in the first step with a compound of formula (6) and the reaction product of the first step is reacted in a second step with a compound of formula (4) and/or a compound of formula (5)
and wherein the reaction product of the second step is reacted in a third step with
a compound of formula (7) and/or a compound of formula (8)

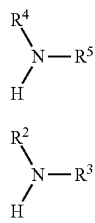

(7)

(8)

wherein $R^2$, $R^3$, $R^4$, $R^5$ have the meaning as defined before,
or
wherein the reaction product of the second step is reacted in a third step with a compound of formula (9) and/or a compound of formula (10)

  H—OR$^9$ (9)

  H—OR$^{10}$ (10)

wherein $R^9$ and $R^{10}$ have the meaning as defined before.

As a cyanuric halide there may be employed the fluoride, chloride or bromide. Cyanuric chloride is preferred. The reaction may be carried out in an aqueous medium, wherein the cyanuric halide is suspended in water or in an aqueous/organic medium or the cyanuric halide is dissolved in a solvent such as acetone.

Compounds of formulae (4) and (5) may be added without dilution or in form of an aqueous or organic solvent solution or in form of an aqueous suspension in one of the first or second step of the preparation process. Compounds of formulae (4) and (5) may be the same compound but may be also different from each other due to different substituents $R^7$, $R^8$, X, Y and different substitution degree m and n. In specific embodiments the compounds of formulae (4) and (5) are different. For example, the compound of formula (4) can be aniline-4-sulphonic acid and the compound of formula (5) can be 4-aminotoluene-2-sulphonic acid. If the amines of formulae (4) and (5) are different they can be reacted with the cyanuric halide at the same time. They can also be reacted sequentially with the cyanuric halide. If the amines of formulae (4) and (5) are different they can be reacted with the cyanuric halide at the same time. They can also be reacted sequentially with the cyanuric halide.

Preferably, the compounds of formulae (4) and (5) are the same, for example 4-aminotoluene-2-sulphonic acid or 3-sulphonic acid-4-ethyl aniline. Preferably, the compounds of formulae (4) and (5) are 4-aminotoluene-2-sulphonic acid.

The compound of formula (6) may be added in the first step if compounds of formulae (4) and/or (5) are added in the second step or the compound of formula (6) may be added in the second step when compounds of formulae (4) and/or (5) are added in the first step of the preparation process. The compound of formula (6) can be used in its free acid form or in its salt form or in mixed salt form. "Free acid" form means that M of the diamine of formula (6) signifies hydrogen.

The reaction product of the second reaction step is reacted in a third reaction step with amines of formulae (7) and (8) or alcohols of formulae (9) and (10). Amines of formulae (7) and (8) or alcohols of formulae (9) and (10) may be added without dilution or in aqueous or organic solution or in form of an aqueous suspension. Compounds of formulae (7) and (8) may be the same compound but may be also different from each other due to different substituents $R^2$, $R^3$, $R^4$, $R^5$. For example, the compound of formula (7) is iminodiacetic acid and the compound of formula (8) is diethanolamine. In another embodiment the compound of formula (7) is diisopropanolamine and the compound of formula (8) is diethanolamine. Compounds of formulae (9) and (10) may be the same compound but may be also different from each other due to different substituents $R^9$ and $R^{10}$. For example, the compound of formula (9) is propanol and the compound of formula (10) is methanol. If the compounds of formulae (7) and (8) or (9) and (10) are different they can be reacted with the reaction product of the second reaction step at the same time. They can also be reacted sequentially.

Preferably, compounds of formulae (7) and (8) are the same, for example diisopropanolamine, diethanolamine or morpholine.

In another preferred embodiment compounds of formulae (9) and (10) are the same, for example ethanol, preferably methanol.

In one embodiment of the method according to the invention reaction steps are carried out in an aqueous medium and in the first step the first halogen of the cyanuric halide is substituted by the amine of formula (4) and/or formula (5), the temperature is maintained in the range of 0° C. to 20° C. and the pH value is maintained in the range of pH=4 to 6. In the second step substitution of the second halogen of the cyanuric halide with an amine of the compound of formula (6) is carried out at a temperature in the range of 20 to 80° C. and the pH value is maintained in the range of pH=6 to 7.5. In the third step substitution of the third halogen of the cyanuric halide with the amine of formula (7) and/or formula (8) is carried out at a temperature in the range of 60° C. to 102° C. and the pH value is maintained in the range pH=7.5 to 9.

Temperature ranges in the respective reaction steps are maintained by cooling or heating the reaction mixture. The pH may be controlled by the addition of suitable acids or bases as necessary, preferred acids being hydrochloric acid, sulfuric acids, formic acid, or acetic acid, preferred bases being alkali metal (lithium, sodium, potassium) hydroxides, carbonates or bicarbonates or aliphatic tertiary amines, e.g. triethanolamine or triisopropanolamine. The pH value can be monitored throughout the reaction process and appropriate amounts of acid or base can be added to the reaction formulation.

The reaction product can be used directly, or after desalting using a membrane filtration process, or the compound of formula (2) according to the invention can be isolated, e.g. by precipitation or phase separation.

If $Z^1$ and $Z^2$ in compound of formula (2) are $NR^2R^3$ and $NR^3R^4$, the aliphatic amines of compounds of formulae (7) and (8) are generally employed in a slight excess to promote the desired conversion of the reactants. If $Z^1$ and $Z^2$ in compound of formula (2) are $OR^9$ and $OR^{10}$, a large excess of compounds of formula (9) and (10) is required.

Generally, the compound of formula (2) according to the invention can be produced by commonly known methods of producing 4,4'-diamino-stilbene-2,2'-disulphonic acid based OBAs.

In a fourth aspect the invention relates to a process for whitening paper comprising the steps of providing a suspension of pulp, adding 0.01 to 5% by weight based on dry fiber of the pulp of an aqueous composition according to the invention to obtain a brightened pulp, draining water from the pulp, pressing and drying the pulp into a paper sheet.

In a fifth aspect the invention relates to a composition for the surface brightening of paper comprising or consisting of at least one surface sizing agent, at least one compound of formula (2) according to the invention as an optical brightening agent, and water.

The surface brightening composition may be between 0.2 and 30 g/l, preferably between 1 and 15 g/l, most preferably between 2 and 12 g/l, based on the total volume of the surface brightening composition.

The surface sizing agent comprises one or more starch materials. The surface sizing agent is typically an enzymatically, chemically or thermally modified starch, e.g. oxidized starch, hydroxyethylated starch or acetylated starch. The starch may also be native starch, anionic starch, a cationic starch, or an amphipathic starch depending on the particular embodiment being practiced. While the starch source may be any, examples of starch sources include corn, wheat, potato, rice, tapioca, and sago.

The amount of the surface sizing agent present in the surface brightening composition is 1% to 30% by weight, preferably 2 to 20% by weight, more preferably 5 to 15% by weight, the weight % being based on the total weight of the surface brightening composition.

The pH value of the surface brightening composition is typically in the range of 4 to 13, preferably 6 to 11.

In addition to the surface sizing agent, the compound of formula (2) and water, the surface brightening composition may contain by-products formed during the preparation of the compound of formula (2) according to the invention as well as other conventional paper additives. Examples of such additives are carriers, e.g. polyvinyl alcohol, defoamers, wax emulsions, dyes, pigments, monovalent metal salts, e.g. sodium chloride, divalent metal salts, e.g. calcium chloride, solubilizing aids, preservatives, complexing agents, cross-linkers, special resins etc.

The surface brightening composition may be applied to the surface of a paper substrate by any surface treatment method known in the art. Examples of application methods include size-press applications, calendar-size applications, tub-sizing, coating applications and spraying applications (see, for example, pages 283-286 in Handbook for Pulp & Paper Technologists by G. A. Smook, $2^{nd}$ Edition Angus Wilde Publications, 1992 and US 2007/0277950.) The preferred method of application is at the size-press such as puddle size-press or rod-metered size-press. A preformed sheet of paper is passed through a two-roll nip which is flooded with the sizing composition. The paper absorbs some of the composition, the remainder being removed in the nip.

The paper substrate contains a web of cellulose fibers which may be synthetic or sourced from any fibrous plant including woody and non-woody sources. Preferably the cellulose fibers are sourced from hardwood and/or softwood. The fibers may be either virgin fibers or recycled fibers, or any combination of virgin and recycled fibers.

The cellulose fibers contained in the paper substrate may be modified by physical and/or chemical methods as described, for example, in Chapters 13 and 15 respectively in Handbook for Pulp & Paper Technologists by G. A. Smook, $2^{nd}$ Edition Angus Wilde Publications, 1992. One example of a chemical modification of the cellulose fiber is the addition of an optical brightener as described, for example, in EP 0 884 312 A1, EP 0 899 373 A1, WO 02/055646 A1, WO 2006/061399 A2, WO 2007/017336 A1, WO 2007/143182 A2, US 2006/0185808, and US 2007/0193707.

In a sixth aspect the invention relates to the preparation of a surface brightening composition by adding at least one compound of formula (2) according to the invention as an optical brightening agent to a preformed aqueous solution of at least one surface sizing agent at a temperature of between 20° C. and 90° C.

The paper substrate containing the surface brightening composition according to the present invention may have any ISO Brightness, including ISO Brightness that is at least 80, at least 90, or at least 95.

The paper substrate containing the surface brightening composition according to the present invention may have any CIE Whiteness, including at least 110, at least 115, at least 120, at least 125, at least 130, at least 135, at least 140, at least 145. The surface brightening composition according to the invention has a tendency to enhance the CIE Whiteness of a paper sheet as compared to conventional surface brightening compositions containing similar levels of optical brightening agents.

The surface brightening composition according to the present invention has a decreased tendency to green paper sheet to which it has been applied as compared to that of conventional surface brightening compositions containing comparable amounts of optical brightening agents. Greening is a phenomenon related to saturation of the paper sheet such that a paper sheet does not increase in CIE-whiteness even as the amount of optical brightening agent is increased. The tendency to green is indicated by the a*-b* diagram, a* and b* being the colour coordinates in the CIE Lab system. Accordingly, the surface brightening composition according to the present invention affords the papermaker the ability to reach higher CIE Whiteness and ISO Brightness.

In a seventh aspect the invention relates to a pigmented coating composition for the surface brightening of paper comprising or consisting of at least one pigment, at least one binder and at least one compound of formula (2) according to the invention as an optical brightener agent, and water.

The pigmented coating composition comprises 10 to 70% by weight, preferably 40 to 60% by weight of white pigment(s), the weight % being based on the total weight of the pigmented coating composition. Although it is possible to produce coating compositions that are free of white pigment(s), the best white substrates for printing are made using opaque coating compositions comprising the white pigments in the afore mentioned amounts.

The white pigment is selected from inorganic pigments, preferably from the group consisting of e.g., aluminium silicates (kaolin, otherwise known as china clay), calcium carbonate (chalk), titanium dioxide, aluminium hydroxide, barium carbonate, barium sulphate, or calcium sulphate (gypsum) or mixtures thereof. Preferably a mixture 10 to 20% by weight of clay and 30 to 40% by weight of chalk is used as white pigment, the % by weight being based on the total weight of the pigmented coating composition. The term "pigment" as used within the context of the present application refers to a water insoluble compound.

The pigmented coating composition comprises the compound of formula (2) according to the invention in an amount typically in the range of 0.01 to 1% by weight of white pigment, preferably in the range 0.05 to 0.5% by weight, the % by weight being based on the total weight of dry white pigment present in the pigmented coating composition.

The binder may be any of those commonly used in the paper industry for the production of coating compositions and may consist of a single binder or of a mixture of primary and secondary binders. The binder is selected from a primary binder comprising one or more of synthetic latex, styrene-butadiene, vinylacetate, styrene acrylic, vinyl acrylic, or ethylene vinyl acetate polymer and optionally a secondary binder comprising one or more of starch, carboxymethylcelulose, casein, soy polymer, polyvinyl alcohol.

The sole or primary binder is preferably a synthetic latex, typically a styrene-butadiene, vinyl acetate, styrene acrylic, vinyl acrylic or ethylene vinyl acetate polymer. The preferred primary binder is a latex binder.

The sole or primary binder is used in an amount typically in the range of 2 to 25% by weight, preferably of 4 to 20% by weight, the % by weight being based on the total weight of white pigment present in the pigmented coating composition.

The secondary binder which may be optionally used may be, e.g., starch, carboxymethylcellulose, casein, soy polymers, polyvinyl alcohol or a mixture thereof. The preferred secondary binder which may be optionally used is a polyvinyl alcohol binder.

The polyvinyl alcohol which may be optionally used in the pigmented coating composition as secondary binder has preferably a degree of hydrolysis greater than or equal to 60% and a Brookfield viscosity of from 2 to 80 mPa·s (4% aqueous solution at 20° C.). More preferably, the polyvinyl alcohol has a degree of hydrolysis greater than or equal to 80% and a Brookfield viscosity of from 2 to 40 mPa·s (4% aqueous solution at 20° C.).

When optionally used, the secondary binder is used in an amount typically in the range of 0.1 to 20% by weight, preferably of 0.2 to 8% by weight, more preferably of 0.3 to 6% by weight, the % by weight being based on the total weight of white pigment, present in the pigmented coating composition.

The pH value of the coating composition is typically in the range of 5 to 13, preferably of 6 to 11, more preferably of 7 to 10. Where it is necessary to adjust the pH of the pigmented coating composition, acids or bases may be employed. Examples of acids which may be employed include but are not restricted to hydrochloric acid, sulphuric acid, formic acid and acetic acid. Examples of bases which may be employed include but are not restricted to alkali metal and alkaline earth metal hydroxide or carbonates, ammonia or amines.

In addition to one or more compounds of formula (2), one or more white pigments, one or more binders, optionally one or more secondary binders and water, the coating composition may contain by-products formed during the preparation of the compound(s) of formula (2) as well as other conventional paper additives. Examples of such additives are for example antifreezers, dispersing agents, synthetic or natural thickeners, carriers, defoamers, wax emulsions, dyes, inorganic salts, solubilizing aids, preservatives, complexing agents, biocides, cross-linkers, pigments, special resins etc.

The coating composition may be prepared by adding the optical brightener of formula (2) according to the invention to a preformed aqueous dispersion of one or more binders, optionally one or more secondary binders and one or more white pigments.

In an eighth aspect the invention relates to a detergent composition for brightening of textiles, carpets or natural fibers comprising or consisting of at least one surfactant and at least one compound of formula (2) according to the invention. The detergent composition can be in liquid or powder form.

The amount of the compound(s) of formula (2) present in the detergent composition may be between 0.005 to 1.0% by weight, more preferably between 0.01 and 0.5% by weight, most preferably between 0.02 and 0.25% by weight, the % by weight being based on the total weight of the detergent composition The detergent composition can further comprise
one or more surfactants, which may be anionic or non-ionic,
one or more builders such as alkali metal polyphosphate, sodium carbonate and zeolites which promote the surfactant behavior by removing calcium and magnesium ions through complexation, precipitation and ion-exchange, respectively,
anti-redeposition agents such as carboxymethylcellulose and poly(vinylpyrrolidone), and
enzymes such as proteases, amylases and lipases.

In addition, the detergent composition may also include pH-adjusting agents (typically, alkali), perfumes, shading dyes, antimicrobial agents, bleaching agents, preservatives, fabric softeners and corrosion inhibitors.

In a ninth aspect the invention relates to the use of compound of formula (2) according to the invention or to the use of the aqueous composition according to the invention for optical brightening of textiles, paper, board and non-wovens. Compound of formula (2) is particularly suitable as an optical brightening agent for the whitening and brightening of paper, board and non-wovens.

The preferred use of compound of formula (2) according to the invention is as an additive in a paper making process wherein the compound of formula (2) is added to pulp.

Another preferred use of compound of formula (2) according to the invention is in a composition for surface brightening of paper according to the invention, or in a pigmented coating composition according to the invention, or in a detergent composition according to the invention.

EXAMPLES

The following shall demonstrate the instant invention in more detail, however, without being limited thereto.

Methods

The optical characteristics of the brightened paper are measured on a calibrated MINOLTA® or AUTOELRE-PHO® spectrophotometer.

CIE Whiteness and ISO Brightness are measured according to ISO 11475 and ISO 2470 respectively.

Schopper-Riegler freeness was determined according to ISO 5267-1.

"Parts" means "parts by weight" if not indicated otherwise. "Dry weight of fiber" means the solid fiber content by weight.

Preparation Example 1

39.3 parts 4-aminotoluene-2-sulphonic acid are added to a stirred suspension of 37.8 parts cyanuric chloride in 343 parts ice water. The pH is kept at 5 by the dropwise addition of 30% sodium hydroxide. The mixture is stirred below 10° C. for 2 hours. 36.5 parts 4,4'-diaminostilbene-2,2'-disulphonic acid are added to the reaction product and 50 parts of water are then added. The pH is adjusted to a range of 6.5 and 7.0 by the addition of 30 weight % sodium hydroxide solution. The mixture is stirred at 75° C. for 3 hours. A solution of 22.4 parts diethanolamine in 22.5 parts water is added, and the mixture is heated at reflux for 3 hours, the pH being kept at 8.0 to 8.5 by the addition of 30% sodium hydroxide. The product is precipitated at room temperature, and isolated by filtration. The filtration residue is a wet press-cake which also contains NaCl generated during the synthesis.

The filtration residue is formulated to an aqueous composition by adding 0.3 parts xanthan gum, 5.4 parts sodium chloride, 0.03 parts Nipacide BIT 20 and 196.4 parts water to obtain 503.9 parts of a light, yellow slurry containing 93.4 parts of the compound of formula (3).

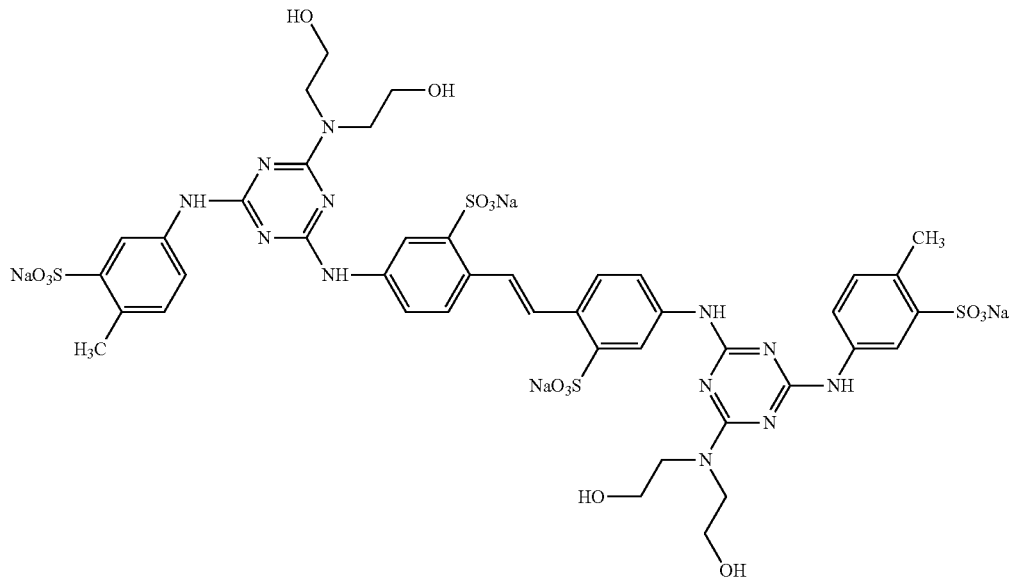

Preparation Examples 2 to 10

The preparation of compounds of Examples 2 to 10 (see Table 1) was made as follows:

39.3 parts 4-aminotoluene-2-sulphonic acid are added to a stirred suspension of 37.8 parts cyanuric chloride in 343 parts ice water. The pH is kept at 5 by the dropwise addition of 30% sodium hydroxide. The mixture is stirred below 10° C. for 2 hours. 36.5 parts 4,4'-diaminostilbene-2,2'-disulphonic acid are added to the reaction product and 50 parts of water are then added. The pH is adjusted to a range of 6.5 and 7.0 by the addition of 30 weight % sodium hydroxide solution. The mixture is stirred at 75° C. for 3 hours. $NHR^2R^3$ and $NHR^4R^5$ (0.22 mol) is added, and the mixture is heated at reflux for 3 hours, the pH being kept at 8.0 to 8.5 by the addition of 30% sodium hydroxide.

Preparation Example 11

39.3 parts 4-aminotoluene-2-sulphonic acid are added to a stirred suspension of 37.8 parts cyanuric chloride in 343 parts ice water. The pH is kept at 5 by the dropwise addition of 30% sodium hydroxide. The mixture is stirred below 10° C. for 2 hours. 36.5 parts 4,4'-diaminostilbene-2,2'-disulphonic acid are added to the reaction product and 50 parts of water are then added. The pH is adjusted to a range of 6.5 and 7.0 by the addition of 30 weight % sodium hydroxide solution. The mixture is stirred at 75° C. for 3 hours. A solution of 189.1 parts methanol in 10 parts water is added, and the mixture is heated at reflux for 10 days, the pH being kept at 8.0 to 8.5 by the addition of 30% sodium hydroxide. Preparation examples 1 to 11 are listed in table 1. The substitution pattern of compounds of examples 2 to 11 is obtained from the schedule of formula (2a) shown below and the entries of table 1.

(2a)

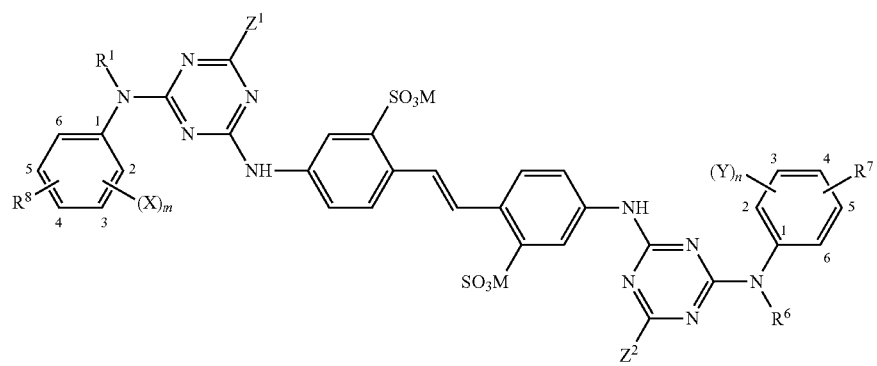

TABLE 1

| Prep. Ex. | Formula | $R^1$, $R^6$ | $Z^1$ $OR^9$ $R^9$ | $Z^1$ $NR^2R^3$ $R^2$ | $Z^1$ $NR^2R^3$ $R^3$ | $Z^2$ $OR^{10}$ $R^{10}$ | $Z^2$ $NR^4R^5$ $R^4$ | $Z^2$ $NR^4R^5$ $R^5$ | $R^7$, $R^8$ position | X, Y position | m, n |
|---|---|---|---|---|---|---|---|---|---|---|---|
| 2 | (11) | H | — | $CH_2CH(OH)CH_3$ | $CH_2CH(OH)CH_3$ | — | $CH_2CH(OH)CH_3$ | $CH_2CH(OH)CH_3$ | $CH_3$, (4) | $SO_3Na$, (3) | 1 |
| 3 | (12) | H | — | $CH_2CH_2CONH_2$ | $CH_2CH_2OH$ | — | $CH_2CH_2CONH_2$ | $CH_2CH_2OH$ | $CH_3$, (4) | $SO_3Na$, (3) | 1 |
| 4 | (13) | H | — | H | $CH_2CH_2SO_3M$ | — | H | $CH_2CH_2SO_3M$ | $CH_3$, (4) | $SO_3Na$, (3) | 1 |
| 5 | (14) | H | — | $CH_2CH_2CH_3$ | $CH_2CH_2CH_3$ | — | $CH_2CH_2CH_3$ | $CH_2CH_2CH_3$ | $CH_3$, (4) | $SO_3Na$, (3) | 1 |
| 6 | (15) | H | — | $CH_2CH_3$ | $CH_2CH_3$ | — | $CH_2CH_3$ | $CH_2CH_3$ | $CH_3$, (4) | $SO_3Na$, (3) | 1 |
| 7 | (16) | H | — | H | $CH(CO_2M)$—$CH_2CO_2M$ | — | H | $CH(CO_2M)$—$CH_2CO_2M$ | $CH_3$, (4) | $SO_3Na$, (3) | 1 |
| 8 | (17) | H | — | $CH_2CO_2M$ | $CH_2CO_2M$ | — | $CH_2CO_2M$ | $CH_2CO_2M$ | $CH_3$, (4) | $SO_3Na$, (3) | 1 |
| 9 | (18) | H | — | $NR^1R^2$ = morpholino | | — | $NR^4R^5$ = morpholino | | $CH_3$, (4) | $SO_3Na$, (3) | 1 |
| 10 | (19) | H | — | $CH_3$ | $CH_2CH_2SO_3M$ | — | $CH_3$ | $CH_2CH_2SO_3M$ | $CH_3$, (4) | $SO_3Na$, (3) | 1 |
| 11 | (20) | H | $CH_3$ | — | — | $CH_3$ | — | — | $CH_3$, (4) | $SO_3Na$, (3) | 1 |

Application Example 1

The aqueous composition of Preparation Example 1 is added at a concentration of 0.2% by weight based on dry fiber (2 kg/ton dry fiber) to a stirred 2.5% aqueous suspension of a 50:50 mixture of bleached softwood and hardwood pulps beaten to a freeness of 20-30° SR (Shopper-Riegler). After stirring for 5 minutes, the pulp suspension is diluted to 0.5% and a paper sheet is made by drawing 1 liter of the dispersed suspension through a wire mesh. After being pressed and dried, the brightened paper is measured for CIE Whiteness and ISO Brightness on a calibrated MINOLTA® spectrophotometer according to ISO 11475 and 2470 respectively.

Application Example 2

The procedure of Application Example 1 is repeated with the difference that the aqueous composition of Example 1 is added at a concentration of 0.4% by weight based on dry fiber (4 kg/ton dry fiber).

Application Example 3

The procedure of Application Example 1 is repeated with the difference that the aqueous composition of Example 1 is added at a concentration of 0.6% by weight based on dry fiber (6 kg/ton dry fiber).

Application Example 4

The procedure of Application Examples 1 to 3 is repeated with the sole difference that compound of formula (12) according to Preparation Example 3 is added in an equivalent active content to the wood pulp instead of compound of formula (3) according to Preparation Example 1 (i.e. same molar concentration of compound of formula (12) compared to compound of formula (3) in Application Examples 1 to 3). The brightened paper is measured for CIE Whiteness and ISO Brightness on a calibrated AUTOELREPHO® spectrophotometer according to ISO 11475 and 2470 respectively.

Application Example 5

The procedure of Application Examples 1, 2, 3 is repeated with the sole difference that compound of formula (11) according to Preparation Example 2 is added in an equivalent active content to the wood pulp instead of compound of formula (3) according to Preparation Example 1 (i.e. same molar concentration of compound of formula (11) compared to compound of formula (3) in Application Examples 1 to 3). The brightened paper is measured for CIE Whiteness and ISO Brightness on a calibrated AUTOELREPHO® spectrophotometer according to ISO 11475 and 2470 respectively.

Application Examples 6

The procedure of Application Examples 1 to 3 is repeated with the sole difference that compound of formula (20) according to Preparation Example 11 is added in an equivalent active content to the wood pulp instead of compound of formula (3) (i.e. same molar concentration of compound of formula (20) compared to compound of formula (3) in Application Examples 1 to 3). The brightened paper is measured for CIE Whiteness and ISO Brightness on a calibrated AUTOELREPHO® spectrophotometer according to ISO 11475 and 2470 respectively.

Comparative Examples 1, 2, 3

The procedure of Application Examples 1 to 3 is repeated with the sole difference that compound of formula (1) is added in an equivalent active content to the wood pulp instead of compound of formula (3) according to Preparation Example 1 (i.e. same molar concentration of compound of formula (1) compared to compound of formula (3) in Application Examples 1 to 3).

Results are shown in Table 2.

TABLE 2

| Example | OBA | OBA conc.[a] | ISO Brightness | L* | a* | b* | CIE Whiteness |
|---|---|---|---|---|---|---|---|
| Appl. Ex 1 | Formula (3) | 2 | 99.6 | 96.97 | 2.22 | −6.45 | 116.6 |
| Appl. Ex 2 | Formula (3) | 4 | 103.1 | 97.32 | 2.73 | −7.25 | 125.3 |
| Appl. Ex 3 | Formula (3) | 6 | 105.0 | 97.40 | 3.02 | −8.38 | 130.4 |
| Comp. Ex 1 | Formula (1) | 2 | 95.9 | 97.09 | 0.89 | −3.07 | 105.2 |
| Comp. Ex 2 | Formula (1) | 4 | 100.6 | 97.27 | 1.59 | −5.84 | 118.1 |
| Comp. Ex 3 | Formula (1) | 6 | 102.4 | 97.21 | 1.85 | −6.79 | 124.5 |
| App. Ex 4 | Formula (12) | 2 | 97.6 | 96.68 | 1.19 | −4.13 | 110.0 |
| App. Ex 4 | Formula (12) | 4 | 102.1 | 96.96 | 1.80 | −6.66 | 121.8 |
| App. Ex 4 | Formula (12) | 6 | 104.2 | 97.32 | 2.00 | −7.49 | 126.3 |
| App. Ex 5 | Formula (11) | 2 | 96.4 | 96.64 | 0.93 | −3.44 | 106.9 |
| App. Ex 5 | Formula (11) | 4 | 100.4 | 96.85 | 1.52 | −5.79 | 117.8 |
| App. Ex 5 | Formula (11) | 6 | 102.8 | 97.00 | 1.86 | −7.14 | 124.1 |
| App. Ex 6 | Formula (20) | 2 | 97.7 | 96.68 | 1.38 | −4.28 | 110.7 |
| App. Ex 6 | Formula (20) | 4 | 101.9 | 96.86 | 2.04 | −6.78 | 122.1 |
| App. Ex 6 | Formula (20) | 6 | 103.8 | 96.97 | 2.33 | −7.87 | 127.2 |

[a]kg OBA per ton paper

Application Example 7

Sizing compositions are prepared by adding an aqueous solution prepared according to Preparation Example 1 at concentrations of 5, 15 and 30 g/l to a stirred, aqueous solution of anionic starch (7.5% w/w) (Perfectamyl A4692) at 60° C. The sizing solution is allowed to cool, then poured between the moving rollers of a laboratory size-press and applied to a commercial 75 g/m2 AKD (alkyl ketene dimer) sized, bleached paper base sheet. The treated paper is dried for 5 minutes at 70° C. in a flatbed drier. The dried paper is allowed to condition, and then measured for CIE Whiteness and ISO Brightness on a calibrated AUTOELREPHO® spectrophotometer according to ISO 11475 and 2470 respectively.

Comparative Example 4

The procedure of Application Example 6 is repeated with the sole difference that compound of formula (1) is added in an equivalent active content to the aqueous solution of starch instead of compound of formula (3) according to Preparation Example 1 (i.e. same molar concentration of compound of formula (1) compared to compound of formula (3) in Application Example 6).

Application Example 8

The procedure of Application Example 7 is repeated with the sole difference that compound of formula (12) according to Preparation Example 3 is added in an equivalent active content to the aqueous solution of starch instead of compound of formula (3) according to Preparation Example 1 (i.e. same molar concentration of compound of formula (12) compared to compound of formula (3) in Application Example 7).

Application Example 9

The procedure of Application Example 7 is repeated with the sole difference that compound of formula (13) according to Preparation Example 4 is added in an equivalent active content to the aqueous solution of starch instead of compound of formula (3) according to Preparation Example 1 (i.e. same molar concentration of compound of formula (13) compared to compound of formula (3) in Application Example 7).
Results are shown in Table 3.

TABLE 3

| Example | OBA | OBA conc[c] | ISO Brightness | L* | a* | b* | CIE Whiteness |
|---|---|---|---|---|---|---|---|
| Appl. Ex 7 | Formula (3) | 5 | 104.3 | 95.70 | 2.81 | −10.31 | 135.3 |
| Appl. Ex 7 | Formula (3) | 10 | 108.4 | 95.97 | 3.31 | −12.47 | 145.3 |
| Appl. Ex 7 | Formula (3) | 15 | 110.3 | 96.07 | 3.46 | −13.47 | 149.9 |
| Appl. Ex 8 | Formula (12) | 5 | 104.0 | 95.69 | 2.81 | −10.15 | 134.5 |
| Appl. Ex 8 | Formula (12) | 10 | 108.1 | 95.90 | 3.34 | −12.40 | 144.9 |
| Appl. Ex 8 | Formula (12) | 15 | 110.1 | 96.08 | 3.52 | −13.36 | 149.4 |
| Appl. Ex 9 | Formula (13) | 5 | 103.7 | 95.66 | 2.88 | −9.98 | 133.7 |
| Appl. Ex 9 | Formula (13) | 10 | 107.8 | 95.87 | 3.49 | −12.30 | 144.4 |
| Appl. Ex 9 | Formula (13) | 15 | 109.9 | 95.99 | 3.76 | −13.46 | 149.6 |
| Comp. Ex 4 | Formula (1) | 5 | 103.6 | 95.66 | 2.77 | −9.94 | 133.6 |
| Comp. Ex 4 | Formula (1) | 10 | 107.8 | 95.91 | 3.33 | −12.21 | 144.1 |
| Comp. Ex 4 | Formula (1) | 15 | 109.7 | 96.04 | 3.52 | −13.18 | 148.5 |

[c]parts OBA per l starch

Application Example 10

A coating composition was prepared containing 70 parts chalk (commercially available under the trade name Hydrocarb 55 from OMYA), 30 parts clay (commercially available under the trade name Polygloss 90 from KaMin), 49.5 parts water, 0.6 parts dispersing agent (commercially available under the trade name Topsperse GX-N from Coatex), 20 parts of 50% latex (a styrene acrylate copolymer commercially available under the trade name Cartacoat B631 from Archroma), 80 parts of 10% polyvinyl alcohol (commercially available under the trade name Mowiol 4-98) and an aqueous solution prepared according to Preparative Example 2 at concentrations of 0.6, 1.2 and 1.8%. The solids content of the coating composition was adjusted to approx. 67% by the addition of water, and the pH was adjusted to 8-9 with sodium hydroxide. The coating composition was then applied to a commercial 75 gsm neutral-sized white paper base sheet using an automatic wire-wound bar applicator with a standard speed setting and a standard load on the bar. The coated paper was then dried for 5 minutes in a hot air flow. Afterwards the paper was allowed to condition and measured for CIE Whiteness and ISO Brightness on a calibrated AUTOELREPHO® spectrophotometer according to ISO 11475 and 2470 respectively.

Application Example 11

The procedure of Application Example 10 is repeated with the sole difference that compound of formula (3) according to Preparation Example 1 is added in an equivalent active content to the color coating instead of compound of formula (11) according to Preparation Example 2 (i.e. same molar concentration of compound of formula (3) compared to compound of formula (11) in Application Example 10).

Application Example 12

The procedure of Application Example 10 is repeated with the sole difference that compound of formula (12) according to Preparation Example 3 is added in an equivalent active content to the color coating instead of compound of formula (11) according to Preparation Example 2 (i.e. same molar concentration of compound of formula (12) compared to compound of formula (11) in Application Example 10).

Comparative Example 5

The procedure of Application Example 9 is repeated with the sole difference that compound of formula (1) is added in an equivalent active content to the color coating instead of compound of formula (11) according to Preparation Example 2 (i.e. same molar concentration of compound of formula (1) compared to compound of formula (11) in Application Example 9).

Results are shown in Table 4

TABLE 4

| Example | OBA | OBA conc[d] | ISO Brightness | L* | a* | b* | CIE Whiteness |
|---|---|---|---|---|---|---|---|
| Appl. Ex 10 | Formula (11) | 0.6 | 98.8 | 95.73 | 2.14 | −6.59 | 118.9 |
| Appl. Ex 10 | Formula (11) | 1.2 | 101.2 | 95.87 | 2.36 | −7.95 | 125.2 |
| Appl. Ex 10 | Formula (11) | 1.8 | 101.5 | 96.02 | 2.08 | −7.91 | 125.3 |
| Appl. Ex 11 | Formula (3) | 0.6 | 98.6 | 95.75 | 1.96 | −6.40 | 118.1 |
| Appl. Ex 11 | Formula (3) | 1.2 | 100.7 | 96.01 | 1.92 | −7.38 | 123.0 |
| Appl. Ex 11 | Formula (3) | 1.8 | 100.6 | 96.17 | 1.32 | −6.94 | 121.4 |
| Appl. Ex 12 | Formula (12) | 0.6 | 96.8 | 95.60 | 1.91 | −5.45 | 113.5 |
| Appl. Ex 12 | Formula (12) | 1.2 | 99.3 | 95.81 | 2.05 | −6.77 | 119.8 |
| Appl. Ex 12 | Formula (12) | 1.8 | 100.1 | 95.98 | 1.76 | −6.99 | 121.2 |
| Comp. Ex 5 | Formula (1) | 0.6 | 96.5 | 95.65 | 1.80 | −5.17 | 112.4 |
| Comp. Ex 5 | Formula (1) | 1.2 | 99.3 | 95.88 | 1.96 | −6.62 | 119.3 |
| Comp. Ex 5 | Formula (1) | 1.8 | 99.5 | 96.09 | 1.31 | −6.38 | 118.7 |

[d]parts OBA/dry parts pigments

The optical brightener of the invention provides significantly higher values of CIE Whiteness and ISO Brightness at equivalent application levels.

The invention claimed is:
1. A compound of formula (2)

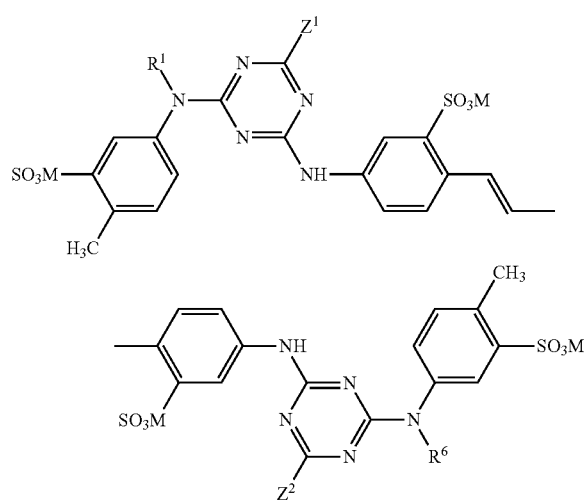

(2)

in which
$Z^1$ and $Z^2$ signify independently from each other $OR^9$ or $OR^{10}$, wherein
$R^9$ and $R^{10}$ signify methyl, or
$Z^1$ and $Z^2$ signify independently from each other $NR^2R^3$ or $NR^4R^5$, wherein
$R^2$ and $R^4$ signify independently from each other hydrogen, linear $C_1$ to $C_3$ alkyl or branched $C_3$ alkyl, linear $C_2$, $C_3$ hydroxyalkyl or branched $C_3$ hydroxyalkyl, $CH_2CO_2M$, or $CH_2CH_2CONH_2$,
$R^3$ and $R^5$ signify independently from each other linear $C_2$ to $C_3$ alkyl or branched $C_3$ alkyl, linear $C_2$, $C_3$ hydroxyalkyl or branched $C_3$ hydroxyalkyl, $CH_2CH_2SO_3M$ $CH_2CO_2M$, or $CH(CO_2M)CH_2CO_2M$, or
$R^2$ and $R^3$
and/or
$R^4$ and $R^5$ signify together with their neighboring nitrogen atom a morpholine ring, and $R^1$ and $R^6$ signify hydrogen, and
M signifies a cation for balancing the anionic charge selected from the group of $Li^+$, $Na^+$, $K^+$, ½ $Ca^{2+}$, ½ $Mg^{2+}$, ammonium which is mono-, di-, tri- or tetrasubstituted by a linear $C_1$ to $C_4$ alkyl or branched $C_3$, $C_4$ alkyl radical, ammonium which is mono-, di-, tri- or tetrasubstituted by a linear $C_1$ to $C_4$ hydroxyalkyl or branched $C_3$, $C_4$ hydroxyalkyl radical, ammonium which is di-, tri-, or tetrasubstituted by a mixture of linear $C_1$ to $C_4$ alkyl or branched $C_3$, $C_4$ alkyl radical or linear $C_1$ to $C_4$ hydroxyalkyl or branched $C_3$, $C_4$ hydroxyalkyl radical, or
M signifies $Na^+$.

2. The compound according to claim 1 wherein
$R^2$ and $R^4$
and/or
$R^3$ and $R^5$ signify independently from each other hydroxyethyl and/or hydroxyisopropyl.

3. A concentrated aqueous composition comprising 5 to 60% by weight of at least one compound of formula (2) according to claim 1.

4. The concentrated aqueous composition according to claim 3 further comprising one or more additives of biocides, thickeners, shading colorants, solubilizers, polymers, or inorganic salt.

5. The aqueous composition according to claim 3 wherein the aqueous composition is a slurry.

6. A process for the preparation of a compound of formula (2) according to claim 1
wherein cyanuric halide is reacted in a first step with
a compound of formula (4)

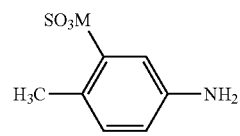

(4)

wherein the reaction product of the first step is reacted in a second step with a compound of the formula (6)

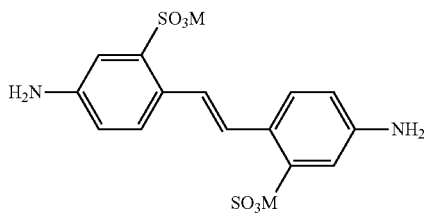
(6)

wherein M has the meaning as defined above,
or wherein cyanuric halide is reacted in a first step with a compound of formula (6) and the reaction product of the first step is reacted in a second step with compounds of formula (4),
and wherein the reaction product of the second step is reacted in a third step with a compound of formula (7) and/or a compound of formula (8)

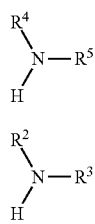
(7)

(8)

wherein $R^2$, $R^3$, $R^4$, $R^5$ have the meaning as defined above, or wherein the reaction product of the second step is reacted in a third step with a compound of formula (9) and/or a compound of formula (10)

$$H\text{—}OR^9 \qquad (9)$$

$$H\text{—}OR^{10} \qquad (10)$$

wherein $R^9$ and $R^{10}$ have the meaning as defined above.

7. The process of claim 6 wherein the reaction is carried out in an aqueous medium and the first step is carried out at a temperature in the range of 0° C. to 20° C. and at a pH value in the range of pH=4 to 6, the second step is carried out at a temperature in the range of 20 to 80° C. and at a pH value in the range of pH=6 to 7.5, and the third step is carried out at a temperature in the range of 60° C. to 102° C. and at a pH value in the range of pH=7.5 to 9.

8. A process for whitening paper comprising the steps:
providing a suspension of pulp,
adding 0.01 to 5% by weight based on dry fiber of the pulp of an aqueous composition according to claim 3 to obtain a brightened pulp,
draining water of the blend, and
pressing and drying the blend into paper sheet.

\* \* \* \* \*